United States Patent [19]
Tanaka et al.

[11] Patent Number: 5,874,592
[45] Date of Patent: Feb. 23, 1999

[54] PHYSIOLOGICALLY ACTIVE SUBSTANCE EI-2128-1

[75] Inventors: Takeo Tanaka; Fumito Koizumi, both of Machida; Tsutomu Agatsuma; Hidemasa Kondo, both of Shizuoka; Yutaka Saitoh, Numazu; Katsuhiko Ando, Machida; Yuzuru Matsuda, Koganei, all of Japan

[73] Assignee: Kyowa Hakko Kogyo Co., Ltd., Tokyo, Japan

[21] Appl. No.: 945,981

[22] PCT Filed: Apr. 2, 1997

[86] PCT No.: PCT/JP97/01135

§ 371 Date: Nov. 12, 1997

§ 102(e) Date: Nov. 12, 1997

[87] PCT Pub. No.: WO97/37034

PCT Pub. Date: Oct. 9, 1997

[30]    Foreign Application Priority Data

Apr. 3, 1996   [JP]   Japan .................................. 8-081753

[51] Int. Cl.$^6$ .................................................. C07D 307/94
[52] U.S. Cl. .......................... 549/331; 549/343; 549/344
[58] Field of Search ...................... 549/331, 343, 549/344

[56]    References Cited

U.S. PATENT DOCUMENTS 5,064,856   11/1991   Garrity et al. .......................... 514/462

FOREIGN PATENT DOCUMENTS 4-59743    2/1992   Japan .
4-74121    3/1992   Japan .
4-202127   7/1992   Japan .

OTHER PUBLICATIONS

The Journal of Antibiotics, vol. 41, No. 12 (Dec. 1988) 1780–1784.
The Journal of Antibiotics, vol. 45, No. 10 (Oct. 1992) 1592–1598.
J. Am. Chem. Soc., vol. 110, No. 24 (1988) 8242–8244.
Tetrahedron Letters, vol. 32, No. 45 (1991) 6613–6616.
Tetrahedron Letters, vol. 34, No. 35 (1993) 5519–5522.
J. Chem. Soc., Perkin Trans., vol. 1, No. 12 (1996) 1385–1393.

*Primary Examiner*—Ba K. Trinh
*Attorney, Agent, or Firm*—Fitzpatrick, Cella, Harper & Scinto

[57]    ABSTRACT

The present invention relates to a novel compound EI-2128-1 having IL-1 production inhibitory activity which is represented by formula (I):

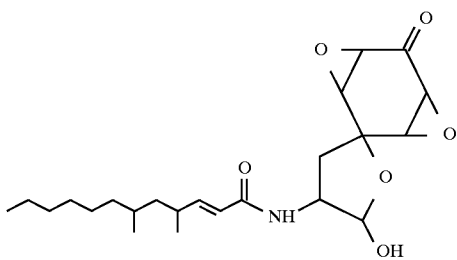

1 Claim, No Drawings

PHYSIOLOGICALLY ACTIVE SUBSTANCE EI-2128-1

This application is a 371 of PCT/JP97/01135 dated Apr. 2, 1997.

TECHNICAL FIELD

The present invention relates to a novel interleukin-1β production inhibiting substance which is produced by a microorganism belonging to the genus Penicillium. The compound has antibacterial activity and interleukin-1 production inhibitory activity and is useful for the treatment of rheumatoid arthritis, gout, osteoarthritis, osteoporosis, periarteritis nodosa, ulcerative colitis, chronic nephritis, active chronic hepatitis, septicemia, endotoxin shock, atherosclerosis, pyrexia of infectious diseases, diffuse scleroderma, and the like.

BACKGROUND ART

Interleukin-1 (hereinafter referred to as IL-1) is a protein having a molecular weight of 17.5 kDa which is produced by a variety of cells in the body such as macrophage, monocyte, neutrophil, fibroblast, skin keratinocyte, hepatic Kupffer cell, renal glomerular mesangial cell, brain astroglia, and angioendothelial cell. IL-1 includes α-form having an isoelectric point (pI) of 5 and β-form having pI of 7. At present, it is known that the α-form and the β-form exhibit the same activity.

IL-1 is known to have various biological activities. That is, IL-1 is deemed to act as a factor that enhances multiplicative division of lymphocytes and as a cofactor that enhances multiplication of B cells and production of antibodies. Further, it is considered that IL-1 acts on arachidonic acid cascade in the temperature center of the hypothalamus to increase the synthesis of prostaglandin $E_2$, thereby causing pyrexia. Furthermore, it is shown that the activity of IL-1 is significantly increased in the serum of patients suffering from septicemia or Crohn's disease and in the cavum articulare of patients who suffer from articular rheumatism. This suggests the participation of IL-1 in the attack and progress of these diseases. Suppression of the production of IL-1 is considered to be effective for alleviating the symptoms that occur through IL-1.

Examples of known compounds having IL-1 production inhibitory activity are synthetic compounds such as naphthalene derivatives (Japanese Published Unexamined Patent Application No. 59743/92), 3-arylisothiazole derivatives (Japanese Published Unexamined Patent Application No. 74121/92), and zingerol derivatives (Japanese Published Unexamined Patent Application No. 202127/92).

There have been reports on aranorosin [J. Antibiot., 41, 1780–1784 (1988), Japanese Published Unexamined Patent Application No. 157386/91], and aranorosinol A and aranorosinol B [J. Antibiot., 45, 1592–1598 (1992)]. However, the structures of these compounds are different from the structure of the compound represented by formula (I), and there has been no report on IL-1 production inhibition by any of these compounds.

DISCLOSURE OF THE INVENTION

The present invention relates to a compound having IL-1 production inhibitory activity which is represented by formula (I):

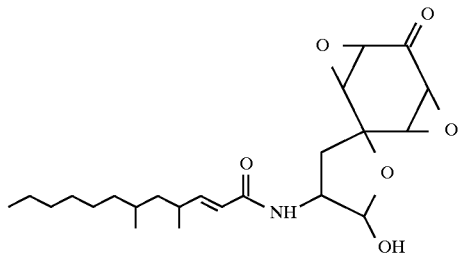

The compound represented by formula (I) is hereinafter referred to as EI-2128-1.

The physicochemical properties of EI-2128-1 are shown below.

The data were obtained by using the following instruments.

Melting point: Yanagimoto, Micro melting point apparatus

Mass spectrum: JEOL LTD., JMS HX/HX110A Mass spectrometer

UV absorption spectrum: Shimadzu Corporation, UV-2200 Ultraviolet spectrophotometer IR absorption spectrum: JEOL LTD., JIR-RFX3001 Infrared spectrophotometer NMR spectrum: JEOL LTD., α400 Nuclear magnetic resonance Specific rotation: Nippon Bunko Kogyo Co., Ltd., DIP-370 Digital polarimeter

Physicochemical Properties of EI-2128-1

Color and form of the substance: White powder

Melting point: 70°–71° C.

Specific rotation: $[\alpha]_D^{27} = +13.9°$ (c=0.17, $CHCl_3$)

Elementary analysis: Found: C, 63.16; H, 8.44; N, 3.29% Calcd. for $C_{23}H_{35}NO_6 \cdot H_2O$: C, 62.85; H, 8.48; N, 3.19%

Mass spectrum: HRFAB-MS Found: 422.2538 $[M+H]^+$ Calcd. for $C_{23}H_{36}NO_6$: 422.2542

Molecular formula: $C_{23}H_{35}NO_6$

UV absorption spectrum: $\lambda_{max}$ ($CH_3OH$); 220 nm (sh)

IR absorption spectrum: $V_{max}$ (KBr); 3390, 1668, 1635, 1539, 984, 930 $cm^{-1}$ NMR spectrum: δ ppm (multiplicity, coupling constant, integration) $^1$H-NMR ($CDCl_3$, 400 MHz) 6.74 (dd, 8.3, 15.4 Hz, 1H), 6.09 (d, 8.1 Hz, 1H), 5.77 (d, 15.4 Hz, 1H), 5.64 (d, 4.6 Hz, 1H), 4.75 (m, 2H), 3.69 (dd, 3.7, 3.9 Hz, 1H), 3.57 (dd, 3.7, 3.9 Hz, 1H), 3.46 (dd, 2.7, 3.9 Hz, 1H), 3.42 (dd, 2.7, 3.9 Hz, 1H), 2.63 (dd, 8.8, 13.1 Hz, 1H), 2.40 (m, 1H), 2.05 (dd, 10.5, 13.1 Hz, 1H), 1.39 (m, 1H), 1.37 (m, 1H), 1.30 (m, 2H), 1.25 (m, 7H), 1.12 (m, 1H), 1.08 (m, 1H), 1.03 (d, 6.8 Hz, 3H), 0.88 (t, 6.8 Hz, 3H), 0.84 (d, 6.6 Hz, 3H) $^{13}$C-NMR ($CDCl_3$, 100 MHz) 198.3 (s), 166.2 (s), 151.9 (d), 121.1 (d), 96.6 (d), 79.1 (s), 64.3 (d), 62.9 (d), 55.9 (d), 55.6 (d), 52.0 (d), 43.9 (t), 37.4 (t), 36.0 (t), 34.2 (d), 31.9 (t), 30.4 (d), 29.7 (t), 26.8 (t), 22.7 (t), 20.5 (q), 19.5 (q), 14.1 (q)

Solubility: Readily soluble in methanol, acetonitrile, and chloroform

Color reaction: Positive to the iodine test and the sulfuric acid test

Thin layer chromatography:

Rf value; 0.71

Developing solvent; chloroform-methanol (85:15)

Thin layer; HPTLC Fertigplatten Kieselgel 60 F254 (Merck & Co., Inc.)

Development; room temperature, ascending method, 20–40 minutes

Detection; coloration with iodine

The activities of EI-2128-1 are described below by Test Examples.

TEST EXAMPLE 1

Inhibitory Activity Against the Production of IL-1

The inhibitory activity of the compound of the present invention, EI-2128-1, against the production of IL-1β by human monocyte-derived THP-1 cells (ATCC No. TIB 202) was examined in the following manner. The amount of IL-1β was determined by the ELISA method.

THP-1 cells were suspended in RPMI1640 medium (Nissui Pharmaceutical Co., Ltd.) containing 10% inactivated fetal calf serum at a concentration of $1 \times 10^5$ cells/ml. The cell suspension was put into wells of a 24-well plate in an amount of 1 ml/well. Phorbol 12-myristate 13-acetate (PMA, final concentration: 30 nM) was added to the wells, followed by incubation in a 5% $CO_2$-incubator at 37° C. for 65 hours to differentiate the cells into macrophage.

Then, the plate was gently washed with serum-free RPMI1640 medium to remove the cells which were not adhered to the wells, and the residue was cultured for 4 hours in serum-free RPMI1640 medium (1 ml/well) containing lipopolysaccharide (LPS, final concentration: 25 μg/ml) and the test compound (final concentration: 0.05–50 μg/ml).

After the completion of culturing, the amount of IL-1β released into the culture supernatant was determined by using an IL-1β determination kit (Amersham Corp.).

The IL-1 production inhibition rate was calculated according to the following equation to obtain $IC_{50}$ (50% inhibitory concentration).

IL-1 production inhibition rate (%)=(A−B)/(A−C)×100

A: Amount of IL-1 produced when only LPS is added

B: Amount of IL-1 produced when LPS and test compound are added

C: Amount of IL-1 produced when LPS is not added

The 50% inhibitory concentration of EI-2128-1 against the IL-1 production by THP-1 cells stimulated by LPS was 0.1 μM.

TEST EXAMPLE 2

Antibacterial Activity Against Various Bacteria

The minimum inhibitory concentration (MIC) of EI-2128-1 against the growth of various bacteria was determined by the agar dilution method using a medium (pH 7.0) comprising 3 g/l Bacto-tryptone (Difco Laboratories Inc.), 3 g/l meat extract, 1 g/l yeast extract, 1 g/l glucose, and 16 g/l agar. The result is shown in Table 1.

TABLE 1

| Test microorganisms | EI-2128-1 MIC (μg/ml) |
| --- | --- |
| *Candida albicans* ATCC 10231 | 42 |
| *Enterococcus hirae* ATCC 10541 | 0.33 |
| *Staphylococcus aureus* subsp. *aureus* ATCC 6538P | 0.33 |
| *Bacillus subtilis* No. 10707 | 0.16 |
| *Proteus vulgaris* ATCC 6897 | 42 |
| *Klebsiella pneumoniae* subsp. *pneumoniae* ATCC 10031 | 21 |

The process for producing EI-2128-1 is described below. EI-2128-1 can be obtained by culturing in a medium a microorganism belonging to the genus Penicillium and having the ability to produce EI-2128-1, allowing EI-2128-1 to accumulate in the culture, and recovering EI-2128-1 from the culture.

As the EI-2128-1-producing strains of the present invention, any strains which belong to the genus Penicillium and have the ability to produce EI-2128-1 can be used. In addition, any mutants of such strains which are obtained by various artificial mutation methods such as UV irradiation, X ray irradiation and treatment with mutagens or by spontaneous mutation may also be used in the present invention, insofar as they have the ability to produce EI-2128-1. A typical example of a suitable strain is Penicillium sp. E-2128 strain.

The mycological properties of Penicillium sp. E-2128 strain are described below.

1. Macroscopic Observation

When the strain is cultured at 25° C. on malt extract agar media, the diameter of a colony reaches 40–46 mm on the seventh day of culturing and about 60 mm on the fourteenth day. On the fourteenth day, the color of the colony is dark greenish blue with a tint of gray and is white to pale blue at the periphery; and the color of the reverse side is pale yellowish white and is cream at the periphery and the center.

When the strain is cultured at 25° C. on potato-glucose agar media, the diameter of a colony reaches about 45 mm on the seventh day of culturing and 70–75 mm on the fourteenth day. On the fourteenth day, the color of the colony is grayish olive, and the color of the reverse side is dark reddish brown.

The growth temperature range for this strain is 6°–38.5° C. and the optimum growth temperature is about 22° C. The pH range which allows its growth is 3–12 and the optimum growth pH is around 7.

2. Optical Microscopic Observation of the Strain When Cultured on a Malt Agar Medium Hyphae are septate, smooth, and colorless to pale yellowish brown, and branch well. Conidiophores are mononematous, smooth, and colorless to pale yellowish brown; they are 1.8–3.5 μm wide and sometimes as long as ca. 160 μm. Penicilli are irregular in shape and size, but many of them are biverticillata-asymmetrica. At the tip of the penicillus, three to four metulae are formed. The metula is cuneiform or rectangular and is 6.5–13.5 μm long and 1.5–3.5 μm wide. Three to six phialides are formed at the tip of the metula. The phialide is lecythiform or lageniform and is 5.5–9.5 μm long and 2–3 μm wide at the widest part and ca. 1.2 μm wide at the tip. The mode of ontogeny of conidia is enteroblastic, and the conidia are formed from the tip of the phialide in catenation. Phialoconidium is single cell type, smooth, globose or subglobose, and 2.5–4.3 μm in diameter; it is colorless to light brown but appears olive brown in a mass. In this strain, the foregoing anamorph alone is observed and no teleomorph is observed.

Taxonomical study of this strain based on the above mycological properties was made according to The Genera of Fungi Sporulating in Pure Culture, 2nd ed., Cramer, Vaduz, J. A. von Arx (1974), and as the result, the strain was classified as Penicillium sp. The strain was named Penicillium sp. E-2128 by the present inventors and was deposited with the National Institute of Bioscience and Human-Technology, Agency of Industrial Science and Technology (1–3, Higashi 1-chome, Tsukuba-shi, Ibaraki, Japan) on Mar. 27, 1996 with accession number FERM BP-5488.

For the culturing of the EI-2128-1-producing strains used in the present invention, conventional methods for culturing filamentous fungi are generally employed. As the medium, either a synthetic medium or a natural medium may be used insofar as it appropriately contains carbon sources, nitrogen sources, inorganic substances, and the like which can be assimilated by the strains employed.

Examples of the carbon sources include carbohydrates such as glucose, fructose, sucrose, stabilose, starch, dextrin, mannose, maltose and molasses; organic acids such as citric acid, malic acid, acetic acid and fumaric acid; alcohols such as methanol and ethanol; hydrocarbons such as methane, ethane, propane and n-paraffins; amino acids such as glutamic acid; and glycerol.

Examples of the nitrogen sources include ammonium salts such as ammonium chloride, ammonium sulfate, ammonium nitrate and ammonium phosphate, amino acids such as aspartic acid, glutamine, cystine and alanine, urea, peptone, meat extract, yeast extract, dry yeast, corn steep liquor, soybean powder, cottonseed cake, soybean casein, casamino acid and Pharmamedia.

Examples of the inorganic substances include potassium monohydrogenphosphate, potassium dihydrogenphosphate, sodium dihydrogenphosphate, magnesium sulfate, ferrous sulfate, manganese sulfate, copper sulfate, cobalt sulfate, zinc sulfate, calcium pantothenate, ammonium molybdate, potassium aluminum sulfate, barium carbonate, calcium carbonate, cobalt chloride and sodium chloride.

If necessary, substances that promote the growth of cells or the production of EI-2128-1 such as vitamins (e.g. thiamine) may be added to the medium. If the strain employed requires specific substances, such substances are also added to the medium.

Culturing is carried out by shaking culture, aeration stirring culture, or the like at 20°–40° C. at pH around neutrality. Usually, by culturing for 3–7 days, the amount of EI-2128-1 accumulated in the culture reaches maximum, and the culturing is completed.

For the isolation and purification of EI-2128-1 from the culture, an ordinary method for isolating a microbial metabolite from the culture can be utilized.

That is, EI-2128-1 can be isolated and purified by extraction of microbial cells with a solvent such as acetone or methanol, removal of microbial cells by filtration or centrifugation, adsorption and desorption of an active substance by column chromatography or thin layer chromatography using an adsorption resin, silica gel, silanised silica gel, reversed-phase silica gel, aluminum, cellulose, diatomaceous earth, magnesium silicate, gel filter medium, an ion exchange resin, etc., partition with a suitable solvent, and the like.

During the above isolation and purification steps, EI-2128-1 can be traced by silica gel thin layer chromatography and then by iodine color development or ultraviolet irradiation at 253.6 nm.

An Example of the present invention is shown below.

BEST MODE FOR CARRYING OUT THE INVENTION

EXAMPLE 1

Penicillium sp. E-2128 strain was used as the seed strain. One loopful of the strain was inoculated into 10 ml of a first medium (pH 6.5) comprising 100 g/l glucose, 30 g/l mashed potatoes (Snow Brand Milk Products Co., Ltd.) and 5 g/l powdery yeast extract S (Nippon Seiyaku Co., Ltd.) in each of three 50-ml test tubes (total amount of the medium: 30 ml). Culturing was carried out with shaking at 25° C. for 4 days.

The resulting first culture (30 ml) was inoculated in 5 ml portions into four 300-ml Erlenmeyer flasks each containing 50 ml of a second medium (total amount of the medium: 200 ml). The composition of the second medium was the same as that of the first medium. Culturing was carried out with shaking at 25° C. for 2 days.

The resulting second culture (200 ml) was inoculated in 5 ml portions into forty 300-ml Erlenmeyer flasks each containing 50 ml of a main fermentation medium (total amount of the medium: 2 l). The composition of the main fermentation medium was as follows: 10 g/l glucose, 10 g/l soluble starch (MS#3600, Japan Maize Products Co., Ltd.), 10 g/l corn starch (Wako Pure Chemical Industries, Ltd.), 5 g/l corn steep liquor, 5 g/l Pharmamedia, 5 g/l Ebios, and 2 g/l calcium carbonate (pH 6.0). Culturing was carried out with shaking at 25° C. for 6 days.

The resulting culture (2 l) was filtered to obtain microbial cells. To the cells was added 2 l of methanol with stirring, followed by filtration. The obtained cell extract (2 l) was diluted with 8 l of water and then passed through a Diaion HP-20 column (400 ml, Mitsubishi Chemical Corporation). After the column was washed with 1.6 l of 50% methanol, elution was carried out with 1.6 l of methanol. The fractions containing EI-2128-1 were combined and diluted with an equal amount of water. This dilution of the fractions was passed through an ODS column (diameter: 3 cm, length: 50 cm, ODS-AQ-S50, YMC), followed by elution with 75% methanol. The fractions containing EI-2128-1 were combined, concentrated to dryness under reduced pressure, and then dissolved in 20 ml of methanol. A 2 ml portion of the resulting solution was passed through HPLC column (D-ODS-5-B S-5 120A, YMC). Elution was carried out with 80% methanol at a flow rate of 20 ml/min, and the EI-2128-1-containing fractions were combined. This purification step by HPLC was repeated, and the EI-2128-1-containing fractions were combined and concentrated to dryness under reduced pressure to give 107 mg of EI-2128-1.

During the above steps, EI-2128-1 was traced by silica gel thin layer chromatography and then by iodine color development or ultraviolet irradiation at 253.6 nm.

INDUSTRIAL APPLICABILITY

The present invention provides a physiologically active substance EI-2128-1 having IL-1 production inhibitory activity.

We claim:

1. Physiologically active substance EI-2128-1 which is represented by formula (I):

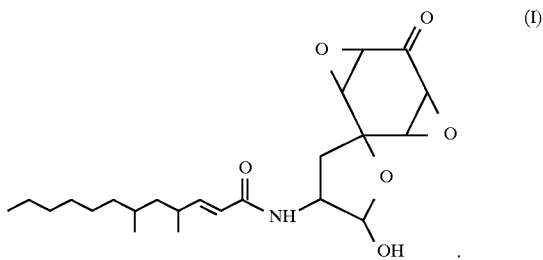

* * * * *